United States Patent [19]

Landscheidt et al.

[11] Patent Number: 5,304,680

[45] Date of Patent: Apr. 19, 1994

[54] PROCESS FOR THE PREPARATION OF AROMATIC AMINES WHICH ARE SUBSTITUTED BY $C_1$-$C_4$-ALKOXY IN THE P-POSITION

[75] Inventors: Heinz Landscheidt, Duisburg; Alexander Klausener, Stolberg; Heinz U. Blank, Odenthal, all of Fed. Rep. of Germany

[73] Assignee: Bayer Aktiengesellschaft, Leverkusen, Fed. Rep. of Germany

[21] Appl. No.: 728,909

[22] Filed: Jul. 10, 1991

[30] Foreign Application Priority Data

Jul. 20, 1990 [DE] Fed. Rep. of Germany ....... 4023056

[51] Int. Cl.$^5$ ............................................. C07C 209/36
[52] U.S. Cl. .................... 564/417; 564/418; 564/428
[58] Field of Search ................. 564/417, 418, 428

[56] References Cited

U.S. PATENT DOCUMENTS 3,953,510  4/1976  Smith et al. ..................... 260/580
4,625,062  11/1986  Nagata et al. ..................... 564/416

FOREIGN PATENT DOCUMENTS 2617808  3/1977  Fed. Rep. of Germany .
2555575  5/1985  France .

OTHER PUBLICATIONS

CA:88:169698m Tsenyuga et al., (1978, Jun.).

Primary Examiner—Glennon H. Hollrah
Assistant Examiner—Brian M. Burn
Attorney, Agent, or Firm—Sprung Horn Kramer & Woods

[57] ABSTRACT

Aromatic amines which are substituted by $C_1$-$C_4$-alkoxy in the p-position are prepared by catalytic hydrogenation of the underlying aromatic nitro compounds in a reaction medium comprising sulphuric acid and a $C_1$-$C_4$-alcohol by a Bamberger type rearrangement at elevated temperature, advantageously by carrying out the catalytic hydrogenation under elevated pressure.

14 Claims, No Drawings

PROCESS FOR THE PREPARATION OF AROMATIC AMINES WHICH ARE SUBSTITUTED BY $C_1$-$C_4$-ALKOXY IN THE P-POSITION

BACKGROUND OF THE INVENTION

1. Field of the Invention

The invention relates to the preparation of aromatic amines which are substituted by $C_1$-$C_4$-alkoxy in the p-position by catalytic hydrogenation of the underlying aromatic nitro compounds in a reaction medium comprising sulphuric acid and a $C_1$-$C_4$-alcohol in the so-called Bamberger type rearrangement.

In the Bamberger rearrangement, p-methoxy-aniline is formed, for example, from phenylhydroxylamine under the action of mineral acids and addition of methanol as the nucleophile. As can be seen from the equation below, it is also possible for water to occupy the p-position as the nucleophile with the formation of p-aminophenol; furthermore, the nucleophilecanalso occupy the o-position with respect to the original hydroxylamine group. For a long time, this Bamberger rearrangement has been associated with the intermediate formation of the hydroxylamine from the underlying nitro compound by catalytic hydrogenation or electrochemical reduction. The mineral acid described most often for this purpose and the only suitable one for industrial applications is sulphuric acid. In such a combination of the hydrogenation of the nitro group with the Bamberger rearrangement, the formation of the not further substituted amino compound from the underlying nitro compound can take place as a further side reaction. These processes can be summarised by the following equations, which exemplify the reduction and reaction of nitrobenzene:

reaction is in general carried out at elevated temperature in order to avoid an even longer reaction.

2. Description of the Related Art

It is known that nitroaromatics, such as, for example, nitrobenzene, 2- and 3-nitro-toluene, 2,3-dinitro-toluene or 6-chloro-2-nitrotoluene, can be reduced electrochemically in methanol and in the presence of sulphuric acid or methylsulphuric acid to give 4-alkoxy-aminoaromatics (see German Offenlegungsschrift 2,617,808, JP 55/154,590, Kagaku Kogyo 56 293-296 (1982)). Processes of this type cause high costs of energy and a considerable investment in apparatus.

Furthermore, it is known that nitroaromatics, such as, for example, 2-chloronitrobenzene, 2-nitro-toluene or 2,6-dimethyl-nitrobenzene, can be reacted in alcoholic solution with addition of water or carboxylic acids at a hydrogen pressure of between 0.01 and 1 bar to give 4-alkoxy-aminoaromatics (see German Offenlegungsschrift 3,443,385 and JP 61/109,759). As is known from the literature, the undesirable formation of p-hydroxyaminoaromatics must be expected in the presence of water in a type of competing conventional Bamberger reaction in aqueous reaction media (see HOUBEN-WEYL VI/lc, 91-92). The addition of carboxylic acids is economically a disadvantage.

It is furthermore known that various nitroaromatics, such as, for example, nitrobenzene, can be reacted in alcoholic solution and in the presence of sulphuric acid with the addition of catalyst poisons, such as, for example, dimethyl sulphoxide, or with the use of modified and deactivated catalysts, such as platinum oxide or platinum sulphide, at pressures of up to 6 bar of hydrogen to give 4-alkoxy-aminoaromatics (SU523,082, SU 520,347, SU 514,811 and SU 578,302 and Nippon Kagaku Kaishi 1237 (1982), 245 (1980) and 1532 (1979)).

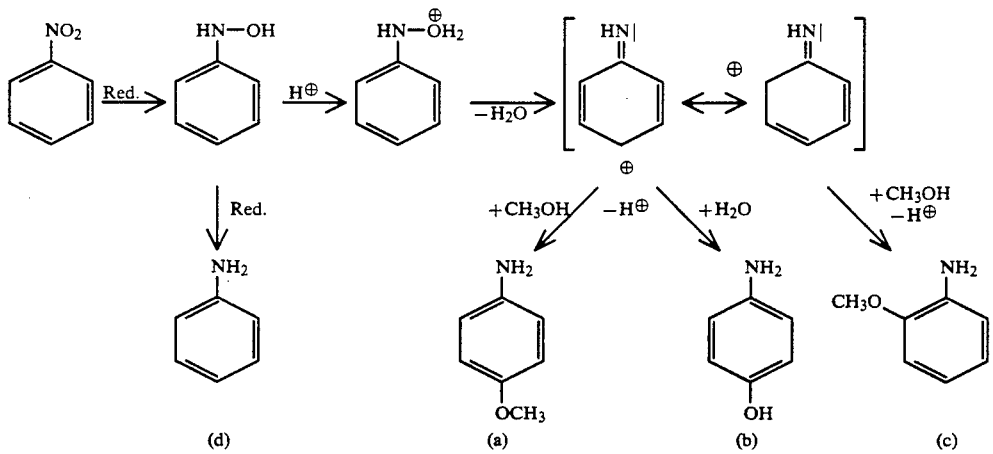

p-Methoxy-aniline (a), which is the product formed in the largest amount in sulphuric acid/methanolic environment, is the generally desired product. In addition, p-aminophenol (b), o-methoxy-aniline (c) and aniline (d) are formed as by-products. The latter (d) is apparently formed here by competition with the Bamberger compound by further reduction of the phenylhydroxylamine.

A further undesired side reaction which takes place is ether formation from the alcohol used, especially since the Bamberger rearrangement which is coupled with the reduction of the nitro compound represents a reaction lasting several hours and even more so, since the Modified catalysts of this type are expensive and in most cases are not or only to a very limited extent reusable, which constitutes a significant economic disadvantage. The addition of moderators or inhibitors, such as dimethyl sulphoxide, moreover makes the workup and purification of the crude reaction products more difficult and results in lengthening of the reaction times, due to deactivation of the noble metal catalysts, and thus in unfavourable space-time yields.

According to the literature, when Bamberger reactions are carried out in alcoholic reaction media for the purpose of preparing p-alkoxy-aminoaromatics, it must be expected that, if higher hydrogen pressures than about 0.2–2 bar of hydrogen pressure are used, the aminoaromatics formed by simple reduction of the nitro groups or even ringhydrogenated compounds are predominantly obtained. In order to prevent this, elevated pressures are in general avoided and in some cases substantially lengthened reaction times are accepted (see German Offenlegungsschrift 3,443,385, JP 53/084,925, 57/072,945 and 57/002,247).

SUMMARY OF THE INVENTION

It has now been found that surprisingly substantial advantages result if this reaction is carried out under elevated pressure, in particular under elevated hydrogen partial pressure and advantageously also at elevated temperature and also in the presence of non-deactivated catalysts. This is surprising, since, according to expert knowledge, under such conditions the beginning of complete hydrogenation of the aromatic ring to give the cycloaliphatic ring should already gain the upper hand. In a further surprising manner, the feared ether formation is also strongly suppressed in the process according to the invention, despite the preferred elevated temperature. The significant advantage of the process according to the invention is the substantial shortening of the reaction time, which is only a fraction of that of processes of the prior art, which significantly increases the utilisation of the apparatus (space-time yield).

A process for the preparation of aromatic amines which are substituted by $C_1$–$C_4$-alkoxy in the p-position of the formula (I)

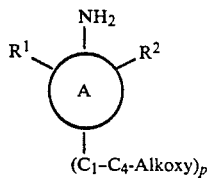

in which

A represents the benzene or the naphthalene ring, p indicates the p-position with respect to the amino group and $R^1$ and $R^2$, independently of one another, denote hydrogen, $C_1$–$C_4$-alkyl, $C_1$–$C_4$-alkoxy or halogen, by catalytic hydrogenation of an aromatic nitro compound in a reaction medium comprising sulphuric acid and a $C_1$–$C_4$-alcohol at elevated temperature has been found, which process is characterized in that the nitro compound which is reacted under elevated pressure, of which hydrogen partial pressure is 1 to 100 bar, in the presence of non-deactivated catalysts from the platinum metal group is one of the formula (II)

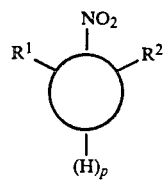

in which A, p, $R^1$ and $R^2$ have the above meaning.

DETAILED DESCRIPTION OF THE INVENTION $C_1$–$C_4$-Alkyl is, for example, methyl, ethyl, propyl, isopropyl, butyl, isobutyl, preferably methyl or ethyl, particularly preferably methyl.

$C_1$–$C_4$-Alkoxy is, for example, methoxy, ethoxy, propoxy, isopropoxy, butoxy, isobutoxy, preferably methoxy or ethoxy, particularly preferably methoxy.

Halogen is, for example, fluorine, chlorine or bromine, preferably chlorine or fluorine.

A $C_1$–$C_4$-alcohol is, for example, methanol, ethanol, propanol, isopropanol, butanol or isobutanol, preferably methanol or ethanol, particularly preferably methanol.

For the reaction medium, 5 to 100 mol, preferably 8 to 80 mol, particularly preferably 10 to 60 mol, of the alcohol are used per mole of the aromatic nitro compound.

The amount of sulphuric acid for the reaction medium is 0.8 to 2.5 mol, preferably 0.9 to 1.5 mol, particularly preferably 1 to 1.3 mol, per mole of the aromatic nitro compound.

The range from 50° to 110° C., preferably 60° to 100° C., particularly preferably 70° to 90° C., is considered elevated temperature.

It is a particular feature of the process according to the invention, that it is carried out under an elevated pressure. To this end, the reaction is carried out in an autoclave, a pressure boiler, a pressure tube or a similar pressure-resistant reaction apparatus, principal features of which are known to one skilled in the art. A pressure of more than 2 bar up to 50 bar may be mentioned as elevated pressure. Of this elevated pressure, the hydrogen partial vapor pressure is at least 1 bar but can also make up the total pressure of up to 50 bar. The difference between 1 bar of hydrogen partial vapor pressure and the total pressure of more than 2 bar is in general the internal pressure of the reaction system, i.e. essentially the vapor pressure of the alcohol and (to a lesser extent) the nitro compound. A further feature, for example when the aromatic nitro compound and the reaction medium is initially introduced in an autoclave, the mixture is flushed with inert gas, such as nitrogen, noble gases, and the like, the autoclave is sealed and heated to the desired reaction temperature, that the pressure in the gas space of the autoclave above the liquid phase increases before the hydrogen required for the reduction is injected at the (partial) pressure according to the invention. In a preferred manner, the hydrogen partial pressure is 3 to 100 bar, in a particularly preferred manner more than 6 to 100 bar.

Suitable catalysts for the process according to the invention are noble metals of the platinum group, in particular platinum itself. The platinum metal, preferably platinum itself, is used with or without support. Examples of supports can be silica gel, alumina or carbon, preferably carbon. The metal deposit on the support is 0.05 to 8% by weight, preferably 0.1 to 6% by weight, particularly preferably 0.25 to 5% by weight of the total catalyst. A compound of the platinum metal which has been placed on the support is reduced to the metal before or during the reaction. The platinum metal is used without a deactivator. Likewise no compounds of a platinum metal which are deactivators themselves are placed on a support. Thus, in particular no sulphur compounds, such as thiophene or dimethyl sulphoxide, are used.

The catalyst with or without support is used in such an amount that 0.001-0.3% by weight, preferably 0.005-0.1% by weight, particularly preferably 0.01-0.1% by weight, of the platinum metal, relative to the nitro compound to be reacted, are present.

The process according to the invention can be carried out using a nitrobenzene or a 1-nitro-naphthalene which can be substituted according to formula (I). In a preferred manner, it is carried out using a substituted or unsubstituted nitrobenzene.

In a preferred manner, p-methoxy- or p-ethoxy-anilines of the formula

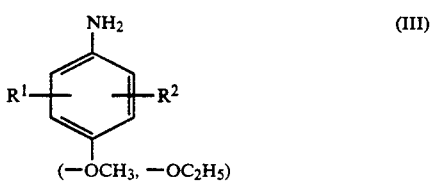

are obtained by reaction of nitrobenzenes of the formula

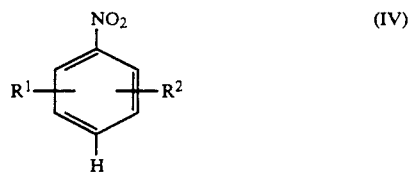

in which in both formulae $R^1$ and $R^2$, independently of one another, denote hydrogen, $C_1-C_4$-alkyl, $C_1-C_4$-alkoxy or halogen, in the presence of methanol or ethanol under the other abovementioned conditions.

In a further preferred manner, the process according to the invention is carried out using an aromatic nitro compound of the formula (I), in which $R^2$ denotes hydrogen.

The reaction according to the invention of o- and m-nitrotoluene or nitrobenzene is very particularly important.

Furthermore, it has proven to be advantageous to recirculate the entire reaction mixture fairly vigorously during the reaction according to the invention, not only in order to increase the reaction rate but also to further increase the selectivity with respect to the desired p-alkoxy-aminoaromatic. This can be achieved by an increased stirring rate, by an increased stroke rate in the case of autoclaves with a reciprocating stirrer, by an increased shaking rate in the case of shaking autoclaves, by an increased recirculation of the hydrogen under elevated pressure using a pump or by other measures having the same effect.

For work-up, the catalyst is filtered off and the filtrate is worked up in a manner known to one skilled in the art by distillation, crystallisation, extraction or chromatography.

In the process according to the invention, the aromatic amines of the formula (I) which are substituted by $C_1-C_4$-alkoxy in the p-position are obtained in high yields in combination with significantly shortened reaction times. The catalyst used in non-deactivated form can be recovered in a particularly simple manner and used repeatedly.

EXAMPLE 1

A mixture of 45.7 g of 3-nitro-toluene (0.333 mol), 40 g of $H_2SO_4$ (98%), 577 g of methanol and 2 g of Pt/carbon catalyst (content 5% of Pt) was hydrogenated in an enamel autoclave at 80° C. and an $H_2$ pressure of 8 bar. $H_2$ absorption was completed after 60 minutes. The reaction mixture was analyzed by high-pressure liquid chromatography and its composition was quantified by comparison with reference substances. The data are given in Table 1.

EXAMPLE 2

Carried out as in Example 1, but at 15 bar of $H_2$ (see Table 1).

EXAMPLE 3

Carried out as in Example 1, but at 25 bar of $H_2$ (see Table 1).

EXAMPLE 4 (FOR COMPARISON)

Carried out as in Example 1, but at 0.5 bar of $H_2$ (see Table 1).

EXAMPLE 5

450 g of methanol, 36.3 g (0.3 mol) of nitrobenzene, 35 g of $H_2SO_4$ (98%) and 0.2 g of Pt/C catalyst (content 5% of Pt) were initially introduced into a 1.5 l enamel autoclave. The mixture was heated to 90° C. with vigorous stirring, and 20 bar of $H_2$ were injected. The hydrogenation was completed after 35 minutes. After the catalyst had been filtered off, the reaction mixture was investigated as in Example 1. The data are given in Table 2.

EXAMPLE 6

Carried out as in Example 5, but at 10 bar of $H_2$ (see Table 2).

EXAMPLE 7 (FOR COMPARISON)

Carried out as in Example 5, but at 1.3 bar of $H_2$ and 3 g of 5% strength Pt/C catalyst (see Table 2).

EXAMPLE 8

350 g of methanol, 21.2 g (0.15 mol) of 2-fluoronitrobenzene, 20 g of sulphuric acid (98%) and 2 g of Pt/C catalyst (content 1% of Pt) were initially introduced into a 1 l glass autoclave.

The mixture was heated to 90° C. with vigorous stirring, and 6 bar of hydrogen were injected.

After 1 hour, the catalyst was filtered off, and the reaction mixture was concentrated on a rotary evaporator. 50 ml of $H_2O$ and 70 ml of 10% strength NaOH were added to the residue, the mixture was extracted 3 times with 100 ml of toluene, the toluene phase was concentrated on a rotary evaporator, and the product was distilled. Yield: 9.5 g of 2-fluoro-4-methoxy-aniline (45% of the theoretical yield).

TABLE 1

(Examples 1-4)

| Example | H₂ partial pressure [bar] | o-Cresidine [%] | m-Toluidine [%] | 2-Methyl-4-amino-phenol [%] | Reaction time [min] | Educt |
| --- | --- | --- | --- | --- | --- | --- |
| 1 | 8.0 | 59.3 | 18.5 | 14.3 | 60 | 0 |
| 2 | 15.0 | 58.8 | 19.7 | 14.0 | 15-30 | 0 |
| 3 | 25.0 | 54.5 | 23.8 | 15.3 | 10 | 0 |
| 4 (comp.) | 0.5 | 56.3 | 6.5 | 13.6 | 510 | 8.5 |

TABLE 2

(Example 5-7)

| Example | H₂ partial pressure | p-NH₂-Anisole (%) | o-NH₂-Anisole (%) | p-NH₂-Phenol (%) | Aniline (%) | Reaction time (min) |
| --- | --- | --- | --- | --- | --- | --- |
| 5 | 20 | 66.4 | 12.1 | 9.2 | 10.2 | 35 |
| 6 | 10 | 64.9 | 11.6 | 8.6 | 12.9 | 60 |
| 7 (comp.) | 1.3 | 56.4 | 10.2 | 8.0 | 23.5 | 230 |

What is claimed is:

1. A process for the preparation of an aromatic amine which is substituted by $C_1-C_4$-alkoxy in the p-position of the formula

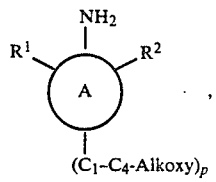

in which
A represents the benzene or the naphthalene ring,
p indicates the p-position with respect to the amino group and
$R^1$ and $R^2$, independently of one another, denote hydrogen, $C_1-C_4$-alkyl, $C_1-C_4$-alkoxy or halogen, by catalytic hydrogenation of an aromatic nitro compound in a reaction medium comprising sulphuric acid and a $C_1-C_4$-alcohol at elevated temperature, wherein the nitro compound which is reacted under elevated pressure of which the hydrogen partial vapor pressure is 6 to 100 bar in the presence of non-deactivated catalysts from the platinum metal group is one of the formula

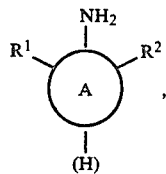

in which A, p, $R^1$ and $R^2$ have the above meaning.

2. The process of claim 1, wherein an aromatic amine which is substituted by $C_1-C_2$-alkoxy in the p-position is prepared by reaction in a reaction medium containing a $C_1-C_2$-alcohol.

3. The process of claim 2, wherein an aromatic amine which is substituted by methoxy in the p-position is prepared by reaction in a reaction medium containing methanol.

4. The process of claim 1, wherein the amount of alcohol is 5 to 100 mol per mole of the aromatic nitro compound.

5. The process of claim 4, wherein the amount of alcohol is 8 to 80 mol per mol of the aromatic nitro compound.

6. The process of claim 5, wherein the amount of alcohol is 10 to 60 mol per mole of the aromatic nitro compound.

7. The process of claim 1, wherein the amount of sulphuric acid is 0.8 to 2.5 mol per mole of the aromatic nitro compound.

8. The process of claim 7, wherein the amount of sulphuric acid is 0.9 to 1.5 mol per mole of the aromatic nitro compound.

9. The process of claim 8, wherein the amount of sulphuric acid is 1 to 1.3 mol per mole of the aromatic nitro compound.

10. The process of claim 1, wherein the elevated temperature is 50° to 110° C.

11. The process of claim 10, wherein the elevated temperature is 60° to 100° C.

12. The process of claim 11, wherein the elevated temperature is 70° to 90° C.

13. The process of claim 2, wherein a p-methoxy- or p-ethoxy-aniline of the formula

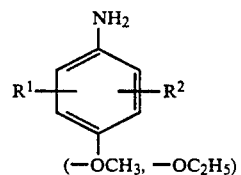

is obtained by reaction of a nitrobenzene of the formula

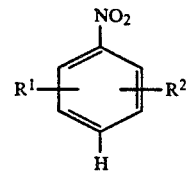

in which both formulae
$R^1$ and $R^2$, independently of one another, denote hydrogen, $C_1-C_4$-alkyl, $C_1-C_4$-alkoxy or halogen, in the presence of methanol or ethanol, respectively.

14. The process of claim 1, wherein the reaction mixture is recirculated vigorously during the reaction.

* * * * *

UNITED STATES PATENT AND TRADEMARK OFFICE
CERTIFICATE OF CORRECTION

PATENT NO. : 5,304,680

DATED : April 19, 1994

INVENTOR(S) : Landscheidt, et al.

It is certified that error appears in the above-identified patent and that said Letters Patent is hereby corrected as shown below:

Col. 7, line 56   Delete " 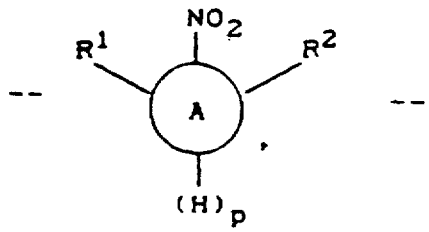 " and substitute

-- --

Signed and Sealed this

First Day of September, 1998

*Attest:*

BRUCE LEHMAN

*Attesting Officer*   *Commissioner of Patents and Trademarks*